United States Patent
Lee et al.

(10) Patent No.: US 6,586,619 B2
(45) Date of Patent: Jul. 1, 2003

(54) PHOTORESIST MONOMER HAVING HYDROXY GROUP AND CARBOXY GROUP, COPOLYMER THEREOF AND PHOTORESIST COMPOSITION USING THE SAME

(75) Inventors: Geun Su Lee, Kyoungki-do (KR); Cha Won Koh, Kyoungki-do (KR); Jae Chang Jung, Kyoungki-do (KR); Min Ho Jung, Kyoungki-do (KR); Ki Ho Baik, Kyoungki-do (KR)

(73) Assignee: Hyundai Electronics Industries Co., Ltd., Ichon-Shi (KR)

( * ) Notice: Subject to any disclaimer, the term of this patent is extended or adjusted under 35 U.S.C. 154(b) by 0 days.

(21) Appl. No.: 10/079,753

(22) Filed: Feb. 19, 2002

(65) Prior Publication Data

US 2002/0091216 A1 Jul. 11, 2002

Related U.S. Application Data

(62) Division of application No. 09/383,861, filed on Aug. 26, 1999, now Pat. No. 6,410,670.

(30) Foreign Application Priority Data

Aug. 26, 1998 (KR) ............................................ 98-34694
Sep. 21, 1998 (KR) ............................................ 98-39079

(51) Int. Cl.[7] .................... C07C 69/74; C07C 69/66; C07C 69/52
(52) U.S. Cl. .................. 560/116; 560/188; 560/205; 562/400; 562/498
(58) Field of Search ................ 560/116, 188, 560/205; 562/400, 498

(56) References Cited

U.S. PATENT DOCUMENTS

| | | |
|---|---|---|
| 3,370,047 A | 2/1968 | Raines |
| 3,715,330 A | 2/1973 | Nogami et al. |
| 4,011,386 A | 3/1977 | Matsumoto et al. |
| 4,106,943 A | 8/1978 | Ikeda et al. |
| 4,126,738 A | 11/1978 | Gaylord |
| 4,202,955 A | 5/1980 | Gaylord |
| 4,440,850 A | 4/1984 | Paul et al. |
| 4,491,628 A | 1/1985 | Ito et al. |
| 4,857,435 A | 8/1989 | Hopf et al. |
| 4,883,740 A | 11/1989 | Schwalm et al. |
| 4,948,856 A | 8/1990 | Minchak et al. |
| 4,986,648 A | 1/1991 | Kobayashi et al. |
| 5,064,919 A | 11/1991 | Hara et al. |
| 5,087,677 A | 2/1992 | Brekner et al. |
| 5,212,043 A | 5/1993 | Yamamoto et al. |
| 5,252,427 A | 10/1993 | Bauer et al. |
| 5,278,214 A | 1/1994 | Moriya et al. |
| 5,324,804 A | 6/1994 | Steinmann |
| 5,585,219 A | 12/1996 | Kaimoto et al. |
| 5,738,975 A | 4/1998 | Nakano et al. |
| 5,843,624 A | 12/1998 | Houlihan et al. |
| 5,849,808 A | 12/1998 | Schacht et al. |
| 5,866,665 A | 2/1999 | Shaffer et al. |
| 6,028,153 A | 2/2000 | Jung |
| 6,045,967 A | 4/2000 | Jung et al. |
| 6,132,926 A | 10/2000 | Jung et al. |
| 6,143,463 A | 11/2000 | Jung et al. |
| 6,150,069 A | 11/2000 | Jung et al. |
| 6,165,672 A | 12/2000 | Jung et al. |
| 6,225,020 B1 | 5/2001 | Jung et al. |
| 6,265,130 B1 | 7/2001 | Lee et al. |
| 6,291,131 B1 | 9/2001 | Jung et al. |
| 6,312,865 B1 | 11/2001 | Jung et al. |
| 6,316,162 B1 | 11/2001 | Jung et al. |
| 6,316,565 B1 | 11/2001 | Jung et al. |
| 6,348,296 B1 | 2/2002 | Jung et al. |
| 6,369,181 B1 | 4/2002 | Jung et al. |
| 6,391,518 B1 | 5/2002 | Jung et al. |

FOREIGN PATENT DOCUMENTS

| | | |
|---|---|---|
| EP | 0071571 | 7/1982 |
| EP | 0 291 970 A2 | 5/1988 |
| EP | 0789278 A2 | 2/1997 |

(List continued on next page.)

OTHER PUBLICATIONS

Massey et al, Brit. Plast. 1969, 42 (4) pp96–98 CA 71:4053.*
Suda et al, Chem. Lett, vol. 3, pp. 389–392.*
N.G. Videnina et al., *J. Appl. Chem,* 1987, 60, 545–548.

(List continued on next page.)

*Primary Examiner*—Alan L. Rotman
*Assistant Examiner*—Hector M Reyes

(57) ABSTRACT

The present invention relates to novel monomers which can be used to form polymers which are useful in a photolithography employing a light source in the far ultraviolet region of the light spectrum, copolymers thereof, and photoresist compositions prepared therefrom. Photoresist monomers of the present invention are represented by the following Chemical Formula 1:

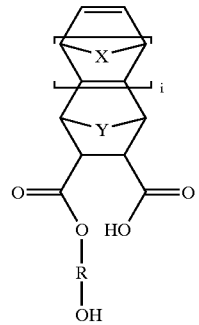

<Chemical Formula 1> wherein,
R is substituted or non-substituted linear or branched ($C_1$–$C_{10}$) alkyl, substituted or non-substituted ($C_1$–$C_{10}$) ether, substituted or non-substituted ($C_1$–$C_{10}$) ester, or substituted or non-substituted ($C_1$–$C_{10}$) ketone;
X and Y are independently $CH_2$, $CH_2CH_2$, oxygen or sulfur; and
i is 0 or an integer of 1 to 2.

9 Claims, No Drawings

FOREIGN PATENT DOCUMENTS

| | | |
|---|---|---|
| EP | 0794458 A2 | 9/1997 |
| EP | 796607 * | 9/1997 |
| EP | 835890 * | 4/1998 |
| EP | 0836119 A1 | 4/1998 |
| EP | 0878738 A2 | 11/1998 |
| FR | 2 757 868 A1 | 7/1998 |
| GB | 768813 | 2/1957 |
| GB | 1329997 | 9/1970 |
| GB | 1342112 | 12/1973 |
| GB | 1484061 | 8/1977 |
| GB | 1335085 | 10/1997 |
| GB | 2320501 A | 6/1998 |
| GB | 2320717 A | 7/1998 |
| GB | 2320718 A | 7/1998 |
| GB | 2321060 A | 7/1998 |
| GB | 2332679 A | 6/1999 |
| GB | 2336845 A | 11/1999 |
| GB | 2336846 A | 11/1999 |
| JP | 57165420 * | 10/1982 |
| NL | 128164 | 11/1977 |
| NL | 1007939 C | 11/1998 |
| WO | WO96/37526 | 11/1996 |
| WO | WO 97/06216 | 2/1997 |
| WO | WO97/33198 | 9/1997 |
| WO | WO 98/07759 | 2/1998 |
| WO | WO 99/14256 | 3/1999 |

OTHER PUBLICATIONS

WPI Abstract No. 99–976491 & JP10316720.

Japanese Abstract Pub. 05297591 pub. Nov. 12, 1993 or Application No. 04099967, 1993.

Jae–Chang Jung et al., "Arf Single Layer Resist Composed of Alicyclic Main Chain Containing Maleic Anhydride," *Journal of Photopolymer Science and Technology*, vol. 10, No. 4 (1997), pp. 529–534.

Kaichiro Nakano, et al., "Chemically Amplified Resist Based on High Etch–Resistant Polymers for 193–nm Lithography," *Journal of Photopolymer Science and Technology*, vol. 10, No. 4 (1997), pp. 561–570.

R.D. Allen et al., "The Influence of Photoacid Structure on the Design and Performance of 193nm Resists," 1997, *Journal of Photopolymer Science and Technology*, vol. 10, 503–510.

F.M. Houlihan et al., "A Commercially Viable 193nm single Layer Resist Platform," 1997, *Journal of Photopolymer Science and Technology*, vol. 10, 511–520.

Thomas I. Wallow, et al., "Evaluation of Cycloolefin–Maleic Anhydride Alternating Copolymers as Single–Layer Photoresist for 193nm Photolithography," *Proc. SPIE*, vol. 2724, 1996, pp. 355–364.

T. Hattori et al., "Synthesis and Dissolution Characteristics of Novel Alicyclic Polymer With Monoacid Ester Structures," *Journal of Photopolymer Science and Technology*, vol. 10, 1997, pp. 535–544.

K. Nozaki and Ei Yaro, "New Protective Groups in Methacrylate Polymer for 193–nm Resists," *Journal of Photopolymer Science and Technology*, vol. 10, 1997, pp. 545–550.

Alexander A. Dobrev et al., "First Application of Funtionalized in the Ester Moiety Acrylates in Diels–Alder Reaction: Influence of Solvents on Stereochemistry," *Bulgarian Chemical Communications*, vol. 28, No. 2 (1995) pp. 253–258.

T.P. McGovern et al., "Mosquito Repellents: Monocarboxylic Esters of Aliphatic Diols;" *Journal of the American Mosqito Control Association*, vol. 4, No. 3, pp. 314–321, 1988.

S. J. Choi et al., "New ArF Single–layer Resist for 193–nm Lithography", 1997, *Journal of Photopolymer Science and Technology*, vol. 10, 521–528.

CA Register No. 100207–98–5, (1998).
CA Register No. 32759–57–2, (1999).
CA Register No. 27056–70–8, (1978).
CA Register No. 174659–58–6, (1998).
CA Register No. 28503–41–5, (1998).
CA Register No. 194997–59–6, (1998).
CA Abstract No. 104:149512 & Macromolecules 19(4) 1266–8 (1986).
CA Abstract No. 91:124064 & Makromol. Chem. 18(8) 1975–88 (1979).
CA Abstract No. 113:24734 & JP 02 051511.
CA Abstract No. 127:227269 & J Photopolym. Sci. Technol. 10(4) 529–534 (1997).
CA Abstract No. 124:317926 & Macromol. Rapid Commun. 17(3) 173–180 (1996).
CA Abstract No. 124:203171 & Macromolecules 29(8) 2755–63 (1996).
CA Abstract No. 127:227308 & Proc. SPIE—Int. Soc. Opt. Eng. (1997) 3049 Advances in Resist Technology and Processing XIV 92–103.
CA Abstract No. 66:18889 & Magy. Kem. Foly. (1966) 72(11)491–3.
CA Abstract No. 199328–07–9, (1998).
CA 1981:47831 Vesti Akad, Navuk BSSR, Ser. Khim. Navuk (1980) 5, pp. 128–130.
Registry No. 37503–43–8, (1998).

D. Braun and Joannis Pomakis, *Uber Die Copolymerisation von Maleinsaureanhydrid Mit Bicyclo [2.2.1] Hept–5–En–2–Carbonsaure*, European Polymer Journal, (1974) vol. 10 [4] pp. 357–365. (Abstract only in English).

J. Byers et al., Recent Advancements in *Cycloolefen Based Resists for ArF Lithography*, Journal of Photopolymer Science and Technology, (1998) vol. II No. 3, pp. 465–474.

James V. Crivello and Sand–Yeon Shim, *Chemically Amplified Electron–Beam Photoresists*, Chemical Mater., (1966) vol. 8, pp. 376–381.

F. M. Houlihan et al., *Photo Generators of Sulfamic Acids; Use in Chemically Amplified Single Layer Resists*, Journal of Photopolymer Science and Technology (1998) vol. 11, No. 3, pp. 419–430.

35–Synthetic High Polymers, *Chemical Abstracts*, (1967) vol. 66, 76325, pp. 7178–7179.

WPI Accession No. 94–227160[28] (FR2695540).
WPI Accession No. 90–049159[07] (JP2003404(elf)).
WPI Accession No. 99–076491 (JP10316720).
Japanese Patent Abstract 10017526.
Japanese Patent Abstract 08134015 A.
CA 121:10910 (JP 05310885).
CA 129:209337 (JP 10–218941), (1998).
CA 129:223219 (JP 10213912), (1998).
CA 1981–47831, (1998).

Uzodinma Okoroanyanwu et al., *New Single Layer Positive Photoresists for 193 nm Photolithography*, SPIE, vol. 3049, 1997, pp. 92–103.

CA 130:229879.
ACS Abstract Ref. 172992–05–1.

* cited by examiner

PHOTORESIST MONOMER HAVING HYDROXY GROUP AND CARBOXY GROUP, COPOLYMER THEREOF AND PHOTORESIST COMPOSITION USING THE SAME

FIELD OF THE INVENTION

The present invention relates to novel monomers used for preparing a photoresist copolymer, copolymers thereof, and photoresist compositions prepared therefrom. More specifically, it relates to such novel monomers, copolymers and photoresist compositions suitable to be exposed to light in the far ultraviolet region of the spectrum.

BACKGROUND OF THE INVENTION

A photosensitive film for use with far ultraviolet light, in particular, for ArF radiation, must satisfy several requisites; it must have low light absorbance at a wavelength of 193 nm, excellent etching resistance and adhesiveness to a substrate, and be developable in an aqueous solution of 2.38% or 2.6% tetramethylammonium hydroxide (hereinafter, abbreviated as TMAH). Up to the present time, researchers have focused on searching for a substance having as high transparency and etching resistance at 193 mn as novolac resins. For example, researchers at the Bell Labs Research Center have enhanced etching resistance of photoresist copolymers by adding an alicyclic unit to the main chain. In addition, researchers at Fujitsu of Japan and Sipri of the United States are actively investigating methacrylate and acrylate compounds as photoresist polymers. However, these techniques have not solved the problem of etching resistance, and involve increased production costs resulting from the introduction of alicyclic groups into the polymer. In addition, the low adhesiveness exhibited by most prior art photoresists is disadvantageous in that photolithographic patterns cannot be established with integrated L/S patterns of 150 nm or less.

SUMMARY OF THE INVENTION

An object of the present invention is to solve the problems described above, and to provide novel monomers which can be used to form copolymers which have excellent adhesiveness and sensitivity, and which can be easily produced at low production cost, and to provide a process for preparing the monomers.

Another object of the present invention is to provide copolymers of the novel monomers, and a process for preparing the same.

Another object of the present invention is to provide photoresist compositions using the copolymers and a process for preparing the same.

Still another object of the present invention is to provide a semiconductor element produced by using the photoresist composition.

The present invention provides a novel compound represented by following Chemical Formula 1:.

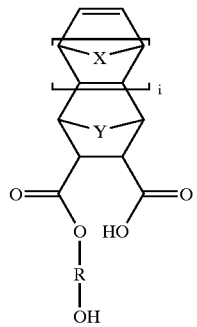

<Chemical Formula 1> wherein,
R is substituted or non-substituted linear or branched ($C_1$–$C_{10}$) alkyl, substituted or non-substituted ($C_1$–$C_{10}$) ether, substituted or non-substituted ($C_1$–$C_{10}$) ester, or substituted or non-substituted ($C_1$–$C_{10}$) ketone;
X and Y are independently $CH_2$, $CH_2CH_2$, oxygen or sulfur; and
i is 0 or an integer of 1 to 2.

In order to achieve other technical objects, photoresist copolymer comprising repeating units of the monomer of Formula 1 are provided by another embodiment of the present invention. Preferred copolymers are represented by following Chemical Formulas 100 and 100a:.

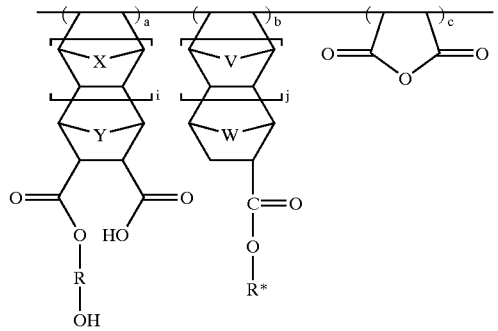

<Chemical Formula 100>

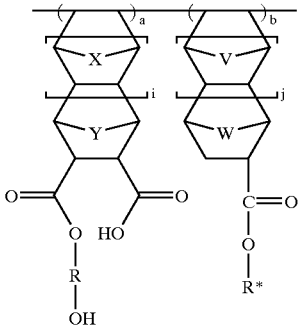

<Chemical Formula 100a> wherein,
R is substituted or non-substituted linear or branched ($C_1$–$C_{10}$) alkyl, substituted or non-substituted ($C_1$–$C_{10}$) ether, substituted or non-substituted ($C_1$–$C_{10}$) ester, or substituted or non-substituted ($C_1$–$C_{10}$) ketone;
X, Y, V and W are independently $CH_2$, $CH_2CH_2$, oxygen or sulfur;
i and j are independently 0 or an integer of 1 to 2;
R* is an acid-reactable group; and a, b and c represent the polymerization ratio of the monomers.

In the case of the chemical formula 100, it is preferred that a:b:c—(0.01–0.2):(0.1–0.4): 0.5 in molar equivalent ratio.

The photoresist composition according to the present invention comprises (i) a photoresist copolymer according to the present invention, a photoacid generator and a conventional organic solvent.

Hereinafter, the present invention will be described in detail.

DETAILED DESCRIPTION

Compounds of Chemical Formula 1 have been found to be particularly useful for preparing chemically amplified photoresist copolymers. Compounds of Chemical Formula 1 have a HYDROXY group which can enhance adhesiveness of the photoresist to a wafer substrate and a carboxylic acid group which can contribute to the enhancement of photosensitivity at the same time. In addition, the compounds can be simply synthesized without toxic odors and are readily crystallized in water without using any complicated separating means such as distillation or column chromatography. Thus, compounds of the present invention are advantageous in mass production at low cost.

In preferred compounds of Chemical Formula 1, R is represented by the following Chemical Formula 1a:

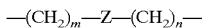

wherein

Z is a moiety of the formula —C($R_1$)($R_2$)— or oxygen;
$R_1$ and $R_2$ are independently H or an ($C_1$–$C_5$) alkyl; and
m and n are independently 0 or an integer of 1 to 5.

The photoresist monomer according to the present invention can be prepared by reacting (i) a di-alcohol such as ethylene glycol, 1,3-propanediol, 1,4-butanediol, 1,5-pentanediol, 2,2-diethyl-1,3-propanediol, 2,2-dimethyl-1,3-propanediol and diethylene glycol and (ii) an anhydride such as 5-norbornene-2,3-dicarboxylic anhydride and exo-3,6-epoxy-1,2,3,6-tetrahydrophthalic anhydride, in an organic solvent such as tetrahydrofuran, dimethylformamide, dioxane, benzene and toluene.

For example, the compound represented by the following Chemical Formula 2, one of the compounds represented by the above Formula 1, can be obtained by reacting a compound of Chemical Formulas 2a and 2b in the presence of an acid catalyst or a base:

<Chemical Formula 2>

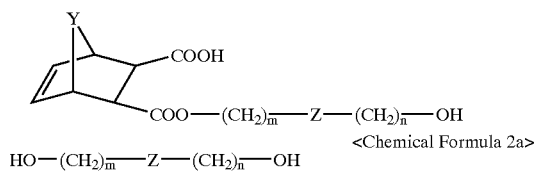

<Chemical Formula 2a>

<Chemical Formula 2b>

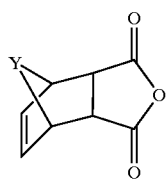

wherein, Y is $CH_2$, $CH_2CH_2$, oxygen or sulfur;
Z is a moiety of the formula —C($R_1$)($R_2$)— or oxygen;
$R_1$ and $R_2$ are independently H or an ($C_1$–$C_5$) alkyl; and
m and n are independently 0 or an integer of 1 to 5.

The compound of Chemical Formula 2a may be used in the same amount or in an excess amount relative to the compound of Chemical Formula 2b.

NaH, KH, $CaH_2$, $Na_2CO_3$, LDA (lithium diisopropylamide) or the like may be used as a base, and sulfuric acid, acetic acid or nitric acid may be used as an acid catalyst.

Novel monomers according to the present invention (the compounds represented by Chemical Formula 1) can also be prepared by a Diels-Alder reaction. For example, the compound represented by the above chemical formula 2 can be prepared by following Reaction Schemes (1) and (2) below:

<Reaction Scheme 1>

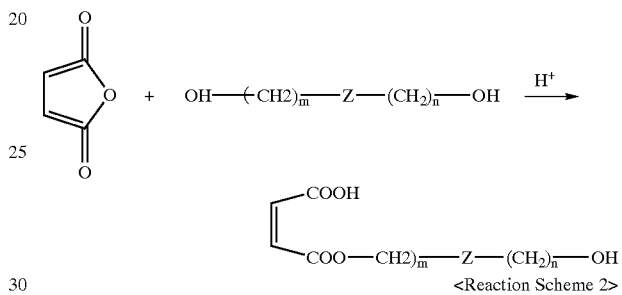

<Reaction Scheme 2>

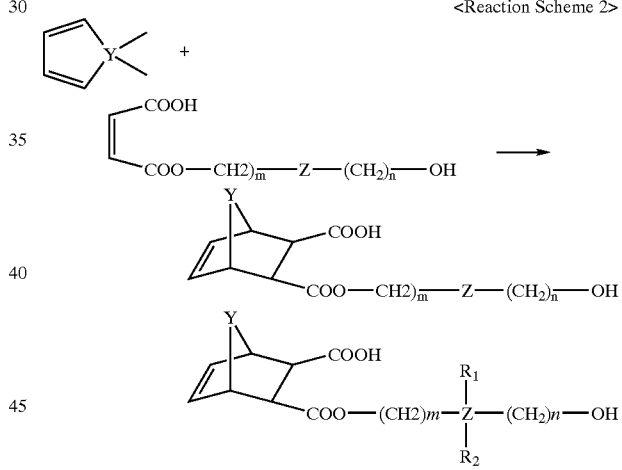

wherein
Y is $CH_2$, $CH_2CH_2$, oxygen or sulfur;
Z is a moiety of the formula —C($R_1$)($R_2$)— or oxygen;
$R_1$ and $R_2$ are independently H or an ($C_1$–$C_5$) alkyl; and
m and n are independently 0 or an integer of 1 to 5.

That is, first, the intermediate material is obtained by reacting maleic anhydride and di-alcohol in an organic solvent such as benzene, tetrahydrofuran, dimethylformamide or dioxane in the presence of an acid catalyst, as shown in the Reaction Scheme 1, and then, the final product material is obtained by a Diels-Alder reaction which is performed in an organic solvent such as benzene and tetrahydrofuran, as shown in the Reaction Scheme 2.

Preferred photoresist copolymers according to the present invention comprise repeating units of a compound of Chemical Formula 1 as a first comonomer and a compound of the following Chemical Formula 3 as the second comonomer:

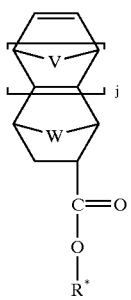

<Chemical Formula 3> wherein,

V and W are independently $CH_2$, $CH_2CH_2$, oxygen or sulfur;

j is 0 or an integer of 1 to 2; and

R* is an acid reactable group.

In the Chemical Formula 3, the R* is released when it is reacted with the acid produced by the photoacid generator in the photoresist composition. Thus, while the photoresist polymer in exposed regions of the photoresist layer becomes soluble in the developing solution, the polymer in the unexposed regions is not dissolved in the developing solution because acid is not generated therein and therefore the acid-reactable groups are still bound to the photoresist polymer. As the result, a predetermined pattern is formed.

Accordingly, the compounds of Chemical Formula 3 have a role in enhancing the photosensitivity of the photoresist polymer by increasing the difference in solubility in the developing solution between the exposed portion and the unexposed portion.

Suitable acid-reactable (acid labile) groups include tert-butyl, 2-tetrahydrofuranyl, 2-tetrahydropyranyl, 2-ethoxyethyl, t-butoxyethyl and so on. In a most preferred embodiment, the second comonomer is tert-butyl-5-norbornene-2-carboxylate, the compound of following Chemical Formula 3a:

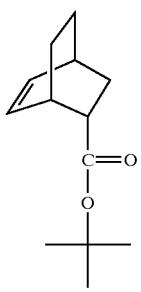

<Chemical Formula 3a>

Maleic anhydride or maleimide derivatives can be added as polymerization-enhancing monomers for making the polymerization between the cycloolefin compounds more efficient. However, when performing polymerization using a metal catalyst, such a polymerization-enhancing monomer is not necessarily required.

The first comonomer of Formula 1 and the second comonomer of Formula 3 comprising the photoresist copolymer according to the present invention each contain substituents having large steric hindrance. Therefore, in preferred copolymers a spacer comonomer, such as the compound of the following Chemical Formula 4, is added to the main polymer chain in order not only to reduce the steric hindrance (thus increasing the synthetic yield, preferably to over 40%), but also to properly adjust the molecular weight to a desirable range (preferably, in the range of 7,000–8,000).

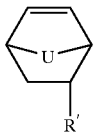

<Chemical Formula 4> wherein,

U is $CH_2$, $CH_2CH_2$, oxygen or sulfur; and

R' is hydrogen or $C_1$–$C_5$ alkyl.

More preferred, the R' is hydrogen or methyl.

The following Chemical Formulas 100, 200, 100a and 200a represent preferred photoresist copolymers according to the present invention.

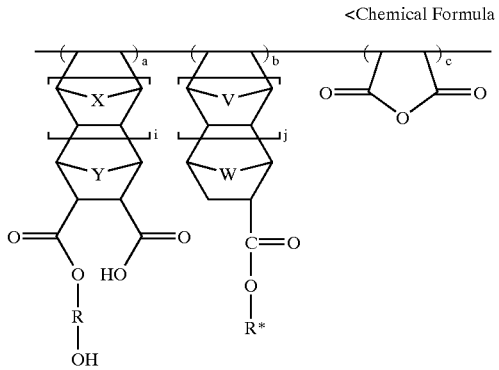

<Chemical Formula 100>

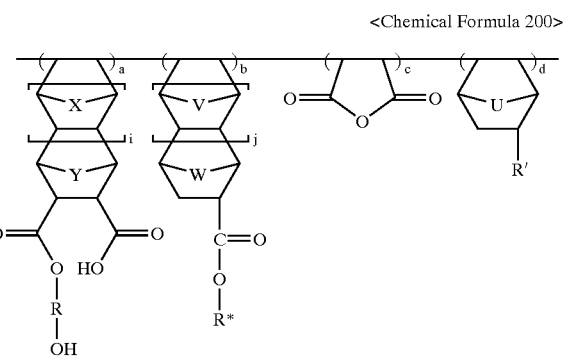

<Chemical Formula 200>

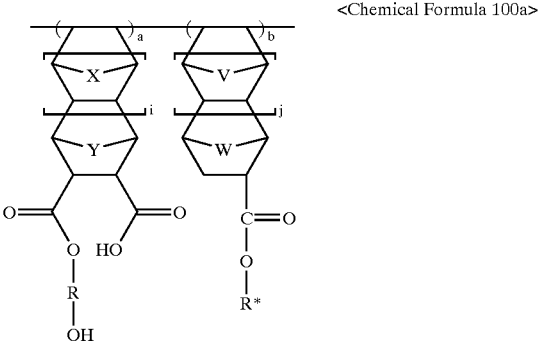

<Chemical Formula 100a>

-continued

<Chemical Formula 200a>

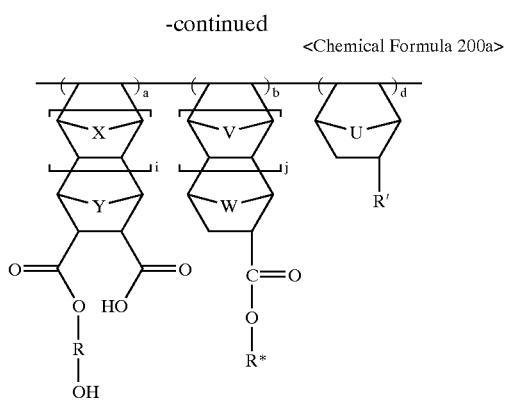

wherein,

X, Y, V, W and U are independently $CH_2$, $CH_2CH_2$, oxygen or sulfur;

R is substituted or non-substituted linear or branched ($C_1$–$C_{10}$) alkyl, substituted or non-substituted ($C_1$–$C_{10}$) ether, substituted or non-substituted ($C_1$–$C_{10}$) ester, or substituted or non-substituted ($C_1$–$C_{10}$) ketone;

R* is an acid-reactable group;

R' is hydrogen or $C_1$–$C_5$ alkyl;

i and j are independently 0 or an integer of 1 to 2; and a, b, c and d are independently the polymerization ratio of the comonomers.

The molecular weight of the photoresist copolymers according the to present invention is 3,000 to 12,000, preferably, 5,000 to 10,000.

While the copolymers represented by the Chemical Formulas 100 and 200 are mainly obtained by a synthesizing method using a polymerization initiator, the copolymers represented by the Chemical Formulas 100a and 200a are mainly obtained by a synthesizing method using a metal catalyst.

A synthesizing method using a polymerization initiator is performed by reacting the comonomers in an organic solvent in the presence of a polymerization initiator. Presently preferred organic solvents include tetrahydrofuran, dimethylformamide, dimethyl sulfoxide, dioxane, methyl ethyl ketone, benzene, toluene or xylene may be used. Conventional radical polymerization initiators, such as 2,2-azobisisobutyronitile (AIBN), acetyl peroxide, lauryl peroxide and tert-butyl peroxide may be used in the synthesis of the copolymers of the present invention.

Photoresist compositions according to the present invention, which are useful for photolithography processes employing a deep ultraviolet light source such as ArF, may be prepared by dissolving a photoresist copolymer according to the present invention together with a conventional photoacid generator in a conventional organic solvent.

Sulfide or onium type compounds are preferably used as the photoacid generator. The photoacid generator may be one or more compounds selected from the group consisting of diphenyl iodide hexafluorophosphate, diphenyl iodide hexafluoroarsenate, diphenyliodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate and dibutylnaphthylsulfonium triflate. The photoacid generator is used in an amount of 0.05 to 10% by weight of the photoresist copolymer employed. If the amount of the photoacid generator is less than 0.05% by weight, photosensitivity of the photoresist becomes poor. On the other hand, if the amount is more than 10%, the photoacid generator readily absorbs deep ultraviolet to provide a pattern having poor cross-sectional surface.

A conventional organic solvent, such as ethyl 3-ethoxypriopionate, methyl 3-methoxypropionate, cyclohexanone, propylene glycol methyl ether acetate, or the like, may be used in the photoresist compositions of the present invention. The amount of solvent used is 200 to 1000% by weight of the photoresist copolymer, in order to obtain a photoresist layer of desirable thickness. According to the experiments by the present inventors, when the amount of solvent is 600% by weight, a photoresist layer having a thickness of 0.5 µm is obtained.

A conventional photoresist pattern-forming method can be used with the photoresist composition prepared according to the present invention, for example as follows:

First, the photoresist composition of the present invention is spin-coated on a silicon wafer to form a thin film, which is then soft-baked (i.e. heated in an oven or on a hot plate at 70 to 200° C., preferably at 80 to 150° C. for 1 to 5 minutes), and exposed to light by using an exposing device employing a deep ultraviolet light source, such as ArF light and KrF light, which has a wavelength below 250 nm. Then, the wafer is post-baked (i.e. heated at 70 to 200° C., more preferably, 100 to 200° C.). Then, the wafer is impregnated in 2.38% aqueous TMAH developing solution for 1.5 minutes, to obtain a photoresist image.

In the above procedure, the exposure energy is preferably 0.1 to 30 mJ/cm² and, instead of the deep ultraviolet light source, an E-beam, X-ray, EUV, VUV(Vacuum Ultra Violet) or similar light source may be used.

By employing the photoresist composition according to the present invention, a line/space (L/S) photoresist pattern having excellent adhesiveness and resolution is obtained, without patten collapse, even when isolation is not more than 70 nm.

According to the present invention, a photoresist composition having excellent etching resistance and adhesiveness can be manufactured in large scale with low production cost, and a semiconductor element having excellent reliability can be prepared therefrom.

DETAILED DESCRIPTION OF PREFERRED EMBODIMENTS

The invention is described in more detail by referring to the examples below, but it should be noted that the present invention is by no means restricted to such examples.

Synthesis of Photoresist Monomer

EXAMPLE 1

Synthesis of 5-norbornene-2-carboxylic acid-3-(2-hydroxyethyl)carboxylate

Ethylene glycol (0.1 mole) is added to 100 ml of tetrahydrofuran, and the mixture is chilled to −20° C. The chilled mixture is stirred for 20–30 minutes in the presence of a basic catalyst, for example, 0.1 mole of sodium hydride. Then, 0.1 mole of 5-norbornene-2,3-dicarboxylic anhydride is slowly added thereto, and the temperature is raised to room temperature to perform the reaction for 24 hours. When the reaction is completed, tetrahydrofuran is distilled off, and the residue is mixed with 0.2 N hydrochloric acid solution (500 ml), and the mixture is crystallized in a refrigerator for several days. Then, the resultant material is filtered, washed with cold water (100 ml), and dried to obtain the compound of Chemical Formula 11 as a pure a colorless solid (19.4 g/yield: 86%).

<Chemical Formula 11>

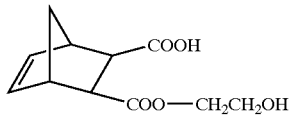

In the process described above, the crystallization step requires a long time (not less than a week). In order to solve the problem, the material resulting from the treatment with hydrochloric acid is extracted with 500 ml of ethyl acetate, dried over a dehydrating agent such as anhydrous magnesium sulfate and filtered. After evaporating the filtrate under reduced pressure, a white solid is obtained, which is then recrystallized from acetone/petroleum ether to provide the compound of Chemical Formula 11 in a pure state (17.6 g/yield: 78%).

EXAMPLE 2

Synthesis of 5-norbornene-2-carboxylic acid-3-(3-hydroxypropyl)carboxylate

The procedure of Example 1 is repeated but using 1,3-propanediol instead of ethylene glycol as a reactant, to obtain the compound of Chemical Formula 12 as a colorless solid (21.1 g/yield: 88%).

<Chemical Formula 12>

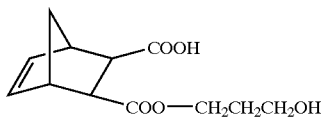

EXAMPLE 3

Synthesis of 5-norbornene-2-carboxylic acid-3-(4-hydroxybutyl)carboxylate

The procedure of Example 1 is repeated but using 1,4-butanediol instead of ethylene glycol as a reactant, to obtain the compound of Chemical Formula 13 as a colorless solid (22.6 g/yield: 89%).

<Chemical Formula 13>

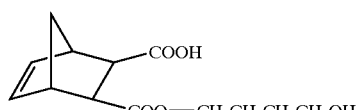

EXAMPLE 4

Synthesis of 5-norbornene-2-carboxylic acid-3-(5-hydroxypentyl)carboxylate

The procedure of Example 1 is repeated but using 1,5-pentanediol instead of ethylene glycol as a reactant, to obtain the compound of Chemical Formula 14 as a colorless solid (22.8 g/yield: 85%).

<Chemical Formula 14>

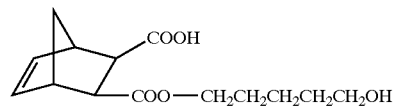

EXAMPLE 5

Synthesis of 5-norbornene-2-carboxylic acid-3-[(2-ethyl-2-hydroxymethyl)butyl]carboxylate The procedure of Example 1 is repeated but using 2,2-diethyl-1,3-propanediol instead of ethylene glycol as a reactant, to obtain the compound of Chemical Formula 15 as a colorless solid (26.9 g/yield: 91%).

<Chemical Formula 15>

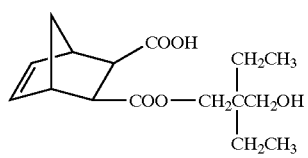

EXAMPLE 6

Synthesis of 5-norbornene-2-carboxylic acid-3-(2,2-dimethyl-3-hydroxypropyl) carboxylate The procedure of Example 1 is repeated but using 2,2-dimethyl-1,3-propanediol instead of ethylene glycol as a reactant, to obtain the compound of Chemical Formula 16 as a colorless solid (24.1 g/yield: 90%).

<Chemical Formula 16>

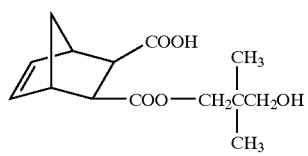

EXAMPLE 7

Synthesis of 5-norbornene-2-carboxylic acid-3-[2-(2-hydroxyethoxy)ethyl]carboxylate The procedure of Example 1 is repeated but using diethylene glycol instead of ethylene glycol as a reactant, to obtain the compound of Chemical Formula 17 as a colorless solid (19.2 g/yield: 71%).

<Chemical Formula 17>

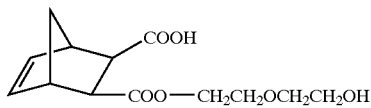

EXAMPLE 8

Synthesis of oxabicyclo[2,2,1]-hept-5-ene-2-carboxylic acid-3-(2-hydroxyethyl) carboxylate Ethylene glycol (0.1 mole) is added to 100 ml of tetrahydrofuran, and the mixture is chilled to −20° C. To the chilled mixture, sodium hydride (0.1 mole) is added, and the resultant mixture is stirred for 20–30 minutes. Then, 0.1 mole of exo-3,6-epoxy-1,2,3,6-tetrahydrophthalic anhydride is slowly added thereto, and the temperature is raised to room temperature to perform the reaction for 24 hours. When the reaction is completed, tetrahydrofuran is distilled off, and the residue is mixed with 0.2 N hydrochloric acid solution (500 ml), and the mixture is crystallized in a refrigerator for several days. Then, the resultant material is filtered, washed with cold water (100 ml), and dried to obtain the compound of Chemical Formula 18 as a colorless solid (19.4 g/yield: 86%).

<Chemical Formula 18>

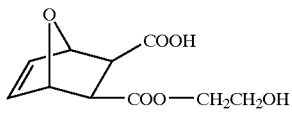

In the process for preparing the compound of Chemical Formula 18 described above, the crystallization step requires a long time of not less than a week. Thus, in order to solve the problem, the material resulting from the treatment with hydrochloric acid is extracted with 500 ml of ethyl acetate, dried over a dehydrating agent such as anhydrous magnesium sulfate, and filtered. After evaporating the filtrate under reduced pressure, a white solid is obtained, which is then recrystallized from acetone/petroleum ether to provide the compound of Chemical Formula 18 in a pure state (17.6 g/yield: 78%).

EXAMPLE 9

Synthesis of oxabicyclo[2,2,1]hept-5-ene-2-carboxylic acid-3-(3-hydroxypropyl) carboxylate.

The procedure of Example 8 is repeated but using 1,3-propanediol instead of ethylene glycol as a reactant, to obtain the compound of Chemical Formula 19 as a colorless solid (20.8 g/yield: 86%).

<Chemical Formula 19>

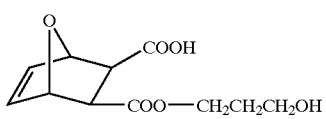

EXAMPLE 10

Synthesis of oxabicyclo[2,2,1]hept-5-ene-2-carboxylic acid-3-(4-hydroxybutyl) carboxylate The procedure of Example 8 is repeated but using 1,4-butanediol instead of ethylene glycol as a reactant, to obtain the compound of Chemical Formula 20 as a colorless solid (22.3 g/yield: 87%).

<Chemical Formula 20>

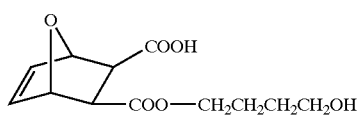

EXAMPLE 11

Synthesis of oxabicyclo[2,2,1]hept-5-ene-2-carboxylic acid-3-hydroxypentyl carboxylate The procedure of Example 8 is repeated but using 1,5-pentanediol instead of ethylene glycol as a reactant, to obtain the compound of Chemical Formula 21 as a colorless solid (23.8 g/yield: 88%).

<Chemical Formula 21>

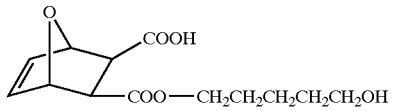

EXAMPLE 12

Synthesis of oxabicyclo[2,2,1]hept-5-ene-2-carboxylic acid-3-[(2-ethyl-2-hydroxymethyl)butyl] carboxylate The procedure of Example 8 is repeated but using 2,2-diethyl-1,3-propanediol instead of ethylene glycol as a reactant, to obtain the compound of Chemical Formula 22 as a colorless solid (27.7 g/yield: 93%).

<Chemical Formula 22>

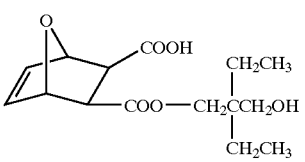

EXAMPLE 13

Synthesis of oxabicyclo[2,2,1]hept-5-ene-2-carboxylic acid-3-(2,2-dimethyl-3-hydroxypropyl) carboxylate The procedure of Example 8 is repeated but using 2,2-dimethyl-1,3-propanediol instead of ethylene glycol as a reactant, to obtain the compound of Chemical Formula 23 as a colorless solid (23.6 g/yield: 86%).

<Chemical Formula 23>

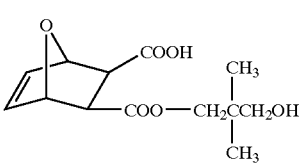

EXAMPLE 14

Synthesis of oxabicyclo[2,2,1]hept-5-ene-2-carboxylic acid-3-[2-(2-hydroxyethoxy)ethyl] carboxylate The procedure of Example 8 is repeated but using diethylene glycol instead of ethylene glycol as a reactant, to obtain the compound of Chemical Formula 24 as a colorless solid (21.2 g/yield: 78%).

<Chemical Formula 24>

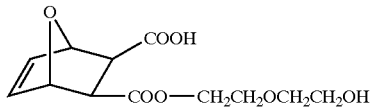

Synthesis of Photoresist Copolymer

EXAMPLE 15

Synthesis of poly(5-norbornene-2-carboxylic acid-3-(2,2-diethyl-3-hydroxypropyl] carboxylate/tert-butyl 5-norbornene-2-carboxylate/maleic anhydride)

5-Norbornene-2-carboxylic acid-3-(2,2-diethyl-3-hydroxypropyl) carboxylate(0.2 mole), tert-butyl 5-norbornene-2-carboxylate(0.8 mole) and maleic anhydride (1.0 mole) are dissolved in tetrahydrofuran. Then, 0.5 to 10 g of AIBN (azobisisobutyronitrile) as a polymerization initiator is added thereto, and the resultant mixture is reacted at about 60–70° C. for 4 to 24 hours under nitrogen or argon atmosphere.

The polymer thus obtained is precipitated from ethyl ether or hexane, and dried to obtain the following compound of Chemical formula 101 (yield: 39%).

<Chemical Formula 101>

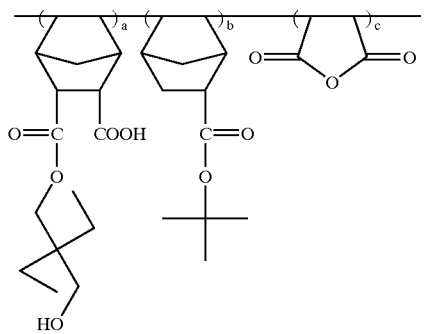

EXAMPLE 16

Synthesis of poly(mono-2-ethyl-2-hydroxymethylbutyl bicyclo[2,2,2]oct-5-ene-2,3-dicarboxylate)/tert-butyl 5-norbornene-2-carboxylate/maleic anhydride]

The procedure of Example 15 is repeated but using mono-2-ethyl-2-hydroxymethylbutyl bicyclo[2,2,2]oct-5-ene-2,3-dicarboxylate (0.2 mole) instead of 5-norbornene-2-carboxylic acid-3-(2,2-diethyl-3-hydroxypropyl) carboxylate (0.2 mole), to obtain the compound represented by the following Chemical Formula 102. (yield: 36%).

<Chemical Formula 102>

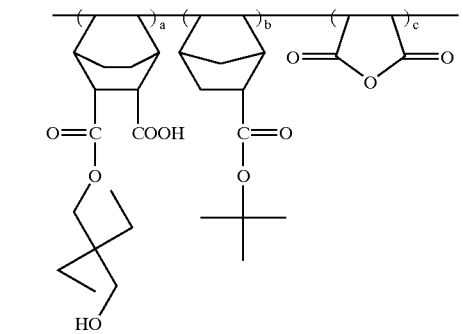

EXAMPLE 17

Synthesis of poly(5-norbornene-2-carboxylic acid-3-(2,2-diethyl-3-hydroxypropyl) carboxylate/tert-butyl bicyclo[2,2,2]oct-5-endo-2-carboxylate/maleic anhydride)

The procedure of Example 15 is repeated but using tert-butyl bicyclo[2,2,2]oct-5-endo-2-carboxylate (0.8 mole) instead of tert-butyl 5-norbornene-2-carboxylate (0.8 mole), to obtain the following compound represented by Chemical Formula 103. (yield: 38%).

<Chemical Formula 103>

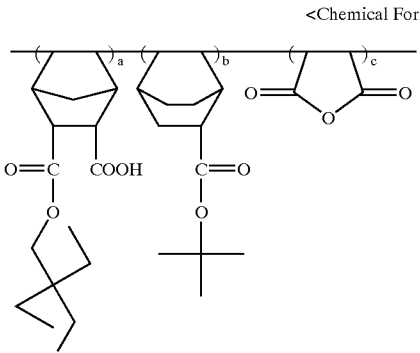

EXAMPLE 18

Synthesis of poly[(mono-2-ethyl-2-hydroxymethylbutyl bicyclo[2,2,2]oct-5-ene-2,3-dicarboxylate)/tert-butyl bicyclo[2,2,2]oct-5-endo-2-carboxylate/maleic anhydride]]

The procedure of Example 16 is repeated but using tert-butyl bicyclo[2,2,2]oct-5-endo-2-carboxylate (0.8 mole) instead of tert-butyl 5-norbornene-2-carboxylate (0.8 mole), to obtain the following compound represented by Chemical Formula 104. (yield: 42%).

<Chemical Formula 104>

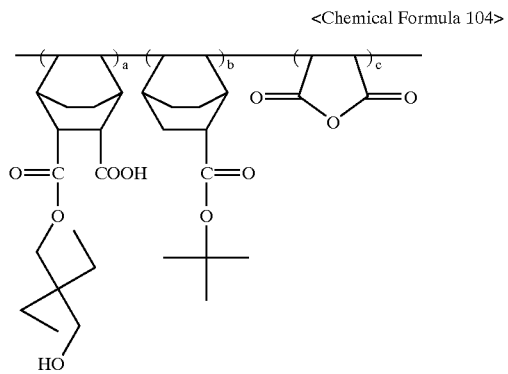

EXAMPLE 19

Synthesis of poly(5-norbornene-2-carboxylic acid-3-(2-hydroxyethyl) carboxylate/tert-butyl-5-norbornene-2-carboxylate/maleic anhydride/norbornene)

In 25 ml of tetrahydrofuran, 5-norbornene-2-carboxylic acid-3-(2-hydroxyethyl)carboxylate (10 mmol), maleic anhydride (100 mmol), norbornene (20 mmol), tert-butyl-5-norbornene-2-carboxylate (70 mmol) and AIBN (0.30 g) are dissolved, and the solution is reacted at 65° C. for 10 hours. When the reaction is completed, the reaction mixture is poured into a solvent for crystallization, such as petroleum ether, to obtain a pure solid, which is then filtered off and dried to give the compound of Chemical Formula 105. (11.3 g/yield: 42%).

<Chemical Formula 105>

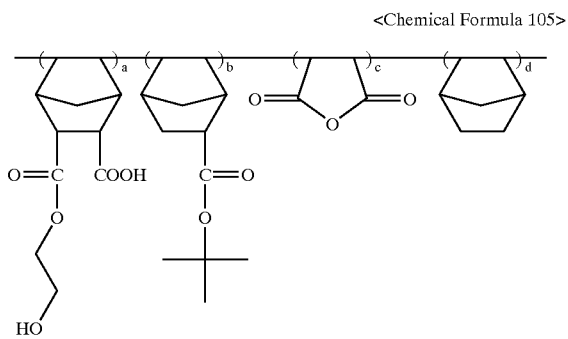

EXAMPLE 20

Synthesis of poly(5-norbornene-2-carboxylic acid-3-(3-hydroxypropyl) carboxylate/tert-butyl-5-norbornene-2-carboxylate/maleic anhydride/norbornene)

The procedure of Example 19 is repeated but using 5-norbornene-2-carboxylic acid-3-(3-hydroxypropyl) carboxylate as a reactant, instead of 5-norbornene-2-carboxylic acid-3-(2-hydroxyethyl) carboxylate, to obtain the compound represented by Chemical Formula 106 as a colorless solid (11.58 g/yield: 41%).

<Chemical Formula 106>

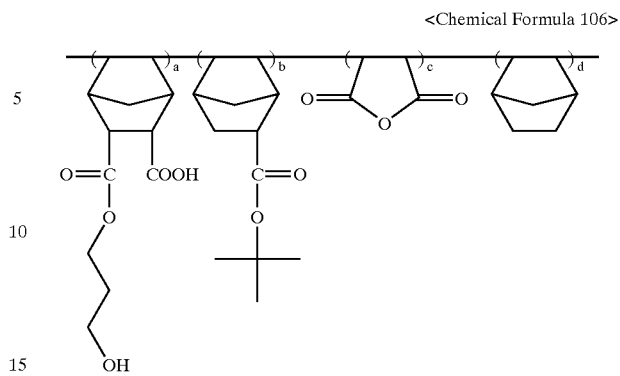

EXAMPLE 21

Synthesis of poly(5-norbornene-2-carboxylic acid-3-hydroxybutyl carboxylate/tert-butyl-5-norbornene-2-carboxylate/maleic anhydride/norbornene)

The procedure of Example 19 is repeated but using 5-norbornene-2-carboxylic acid-3-hydroxybutyl carboxylate as a reactant, instead of 5-norbornene-2-carboxylic acid-3-hydroxyethyl carboxylate to obtain the compound represented by Chemical Formula 107 as a colorless solid (11.36 g/yield: 40%).

<Chemical Formula 107>

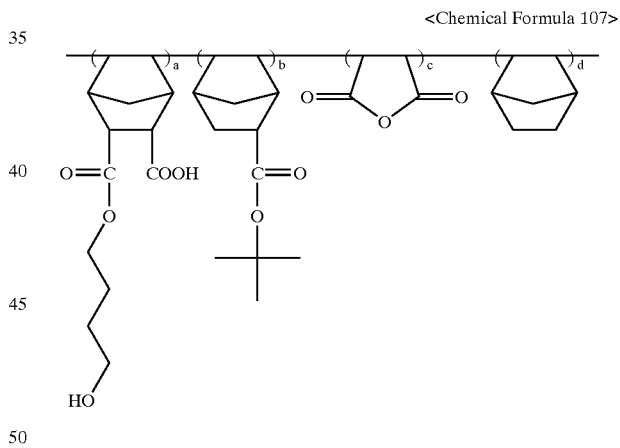

EXAMPLE 22

Synthesis of poly(5-norbornene-2-carboxylic acid-3-hydroxypentyl carboxylate/tert-butyl-5-norbornene-2-carboxylate/maleic anhydride/norbornene)

The procedure of Example 19 is repeated but using 5-norbornene-2-carboxylic acid-3-hydroxypentyl carboxylate as a reactant, instead of 5-norbornene-2-carboxylic acid-3-hydroxyethyl carboxylate to obtain the compound represented by following Chemical Formula 108 as a colorless solid (11.7 g/yield: 41%).

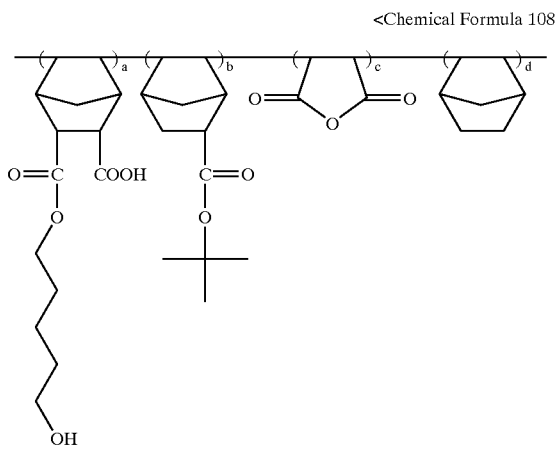

<Chemical Formula 108>

EXAMPLE 23

Synthesis of poly(5-norbornene-2-carboxylic acid-3-(2-ethyl-2-hydroxymethyl)butyl carboxylate/tert-butyl-5-norbornene-2-carboxylate/maleic anhydride/norbornene)

The procedure of Example 19 is repeated but using 5-norbornene-2-carboxylic acid-3-(2,2,-diethyl)hydroxypropyl carboxylate as a reactant, instead of 5-norbornene-2-carboxylic acid-3-hydroxyethyl carboxylate to obtain the compound represented by following Chemical Formula 109 as a colorless solid (27.6 g/yield: 45%).

<Chemical Formula 109>

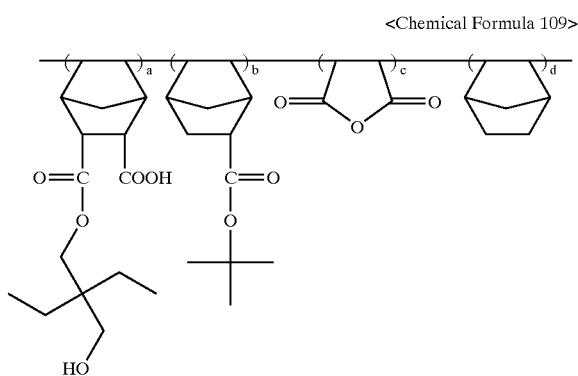

EXAMPLE 24

Synthesis of poly(5-norbornene-2-carboxylic acid-3-(2,2-dimethyl)hydroxypropyl carboxylate/tert-butyl-5-norbornene-2-carboxylate/maleic anhydride/norbornene)

The procedure of Example 19 is repeated but using 5-norbornene-2-carboxylic acid-3-(2,2,-dimethyl)hydroxypropyl carboxylate as a reactant, instead of 5-norbornene-2-carboxylic acid-3-hydroxyethyl carboxylate to obtain the compound represented by following Chemical Formula 110 as a colorless solid (11.7 g/yield: 43%).

<Chemical Formula 110>

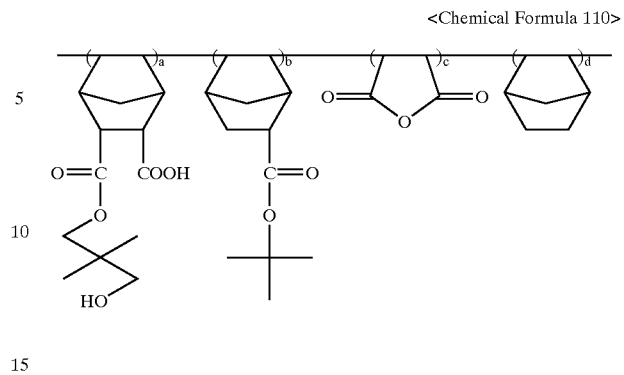

EXAMPLE 25

Synthesis of poly(5-norbornene-2-carboxylic acid-3-(2-hydroxyethoxy)ethyl carboxylate/tert-butyl-5-norbornene-2-carboxylate/maleic anhydride/norbornene)

The procedure of Example 19 is repeated but using 5-norbornene-2-carboxylic acid-3-(2-ethoxy)ethanol carboxylate as a reactant, instead of 5-norbornene-2-carboxylic acid-3-hydroxyethyl carboxylate to obtain the compound represented by following Chemical Formula 111 as a colorless solid (10.9 g/yield: 39%).

<Chemical Formula 111>

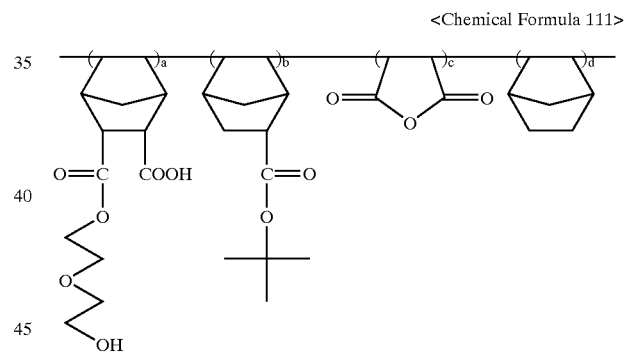

EXAMPLE 26

Synthesis of poly(oxabicyclo[2,2,1]hept-5-ene-2-carboxylic acid-3-hydroxyethyl carboxylate/tert-butyl-5-norbornene-2-carboxylate/maleic anhydride/norbornene)

In 25 ml of tetrahydrofuran, oxabicyclo[2,2,1]oct-5-ene-2-carboxylic acid-3-hydroxyethyl carboxylate (10 mmol), maleic anhydride (100 mmol), norbornene (20 mmol), tert-butyl-5-norbornene-2-carboxylate (70 mmol) and AIBN (0.30 g) are dissolved, and the solution is reacted at 65° C. for 10 hours. After the reaction is completed, the reaction mixture is poured into diethyl ether to obtain a pure solid, which is then dried to give the compound represented by following Chemical Formula 112 (11 g/yield: 41%).

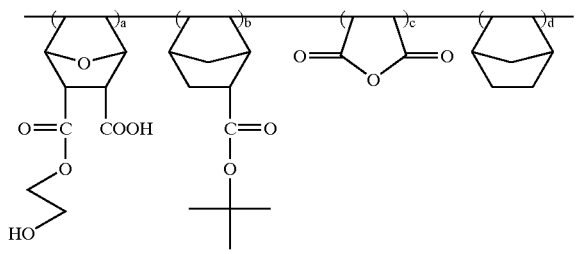

<Chemical Formula 112>

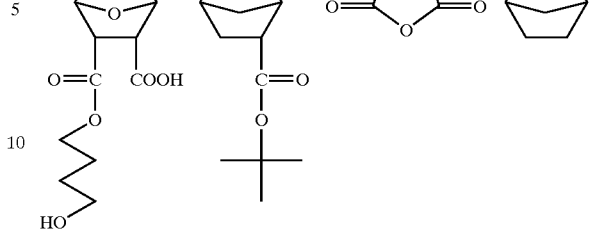

<Chemical Formula 114>

EXAMPLE 27

Synthesis of poly(oxabicyclo[2,2,1]hept-5-ene-2-carboxylic acid-3-hydroxypropyl carboxylate/maleic anhydride/norbornene/tert-butyl-5-norbornene-2-carboxylate)

The procedure of Example 26 is repeated but using oxabicyclo[2,2,1]oct-5-ene-2-carboxylic acid-3-hydroxypropyl carboxylate instead of oxabicyclo[2,2,1]oct-5-ene-2-carboxylic acid-3-hydroxyethyl carboxylate to obtain the compound represented by following Chemical Formula 113 as a colorless solid (11.3 g/yield: 42%).

EXAMPLE 29

Synthesis of poly(oxabicyclo[2,2,1]hept-5-ene-2-carboxylic acid-3-hydroxypentyl carboxylate/tert-butyl-5-norbornene-2-carboxylate/maleic anhydride/norbornene)

The procedure of Example 26 is repeated but using oxabicyclo[2,2,1]oct-5-ene-2-carboxylic acid-3-hydroxypentyl carboxylate as a reactant, instead of oxabicyclo[2,2,1]oct-5-ene-2-carboxylic acid-3-hydroxyethyl carboxylate to obtain the compound represented by following Chemical Formula 115 as a colorless solid (10.9 g/yield: 40%).

<Chemical Formula 113>

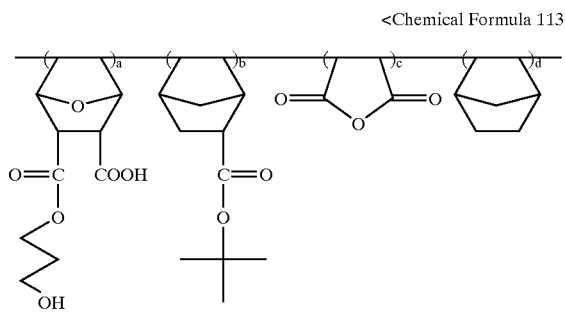

<Chemical Formula 115>

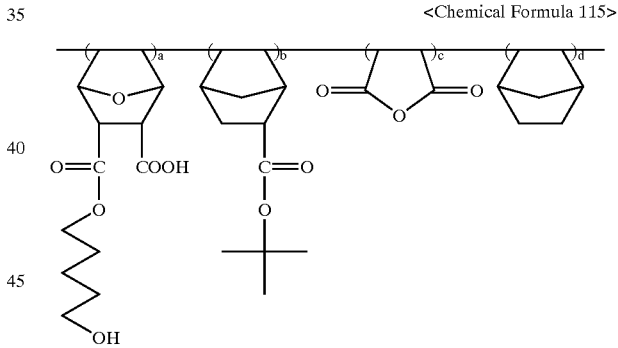

EXAMPLE 28

Synthesis of poly(oxabicyclo[2,2,1]hept-5-ene-2-carboxylic acid-3-hydroxybutyl carboxylate/tert-butyl-5-norbornene-2-carboxylate/maleic anhydride/norbornene)

The procedure of Example 26 is repeated but using oxabicyclo[2,2,1]oct-5-ene-2-carboxylic acid-3-hydroxybutyl carboxylate instead of oxabicyclo[2,2,1]oct-5-ene-2-carboxylic acid-3-hydroxyethyl carboxylate to obtain the compound represented by following Chemical Formula 114 as a colorless solid (11.1 g/yield: 42%).

EXAMPLE 30

Synthesis of poly(oxabicyclo[2,2,1]hept-5-ene-2-carboxylic acid-3-(2,2-diethyl)hydroxypropyl carboxylate/tert-butyl-5-norbornene-2-carboxylate/maleic anhydride/norbornene)

The procedure of Example 26 is repeated but using oxabicyclo[2,2,1]oct-5-ene-2-carboxylic acid-3-(2,2-diethyl)hydroxypropyl carboxylate as a reactant, instead of oxabicyclo[2,2,1]oct-5-ene-2-carboxylic acid-3-hydroxyethyl carboxylate to obtain the compound represented by following Chemical Formula 116 as a colorless solid (12.1 g/yield: 44%).

<Chemical Formula 116>

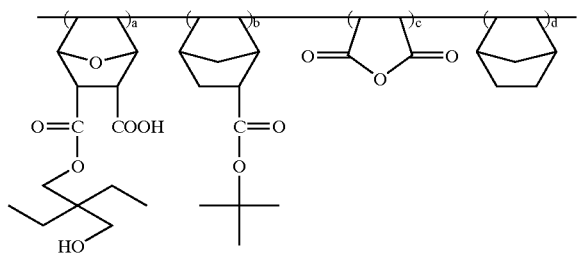

EXAMPLE 31

Synthesis of poly(oxabicyclo[2,2,1]hept-5-ene-2-carboxylic acid-3-(2,2-dimethyl)hydroxypropyl carboxylate/tert-butyl-5-norbornene-2-carboxylate/maleic anhydride/norbornene)

The procedure of Example 26 is repeated but using oxabicyclo[2,2,1]oct-5-ene-2-carboxylic acid-3-(2,2-dimethyl)hydroxypropyl carboxylate as a reactant, instead of oxabicyclo[2,2,1]oct-5-ene-2-carboxylic acid-3-hydroxyethyl carboxylate to obtain the compound represented by following Chemical Formula 117 as a colorless solid (11.7 g/yield: 43%).

<Chemical Formula 117>

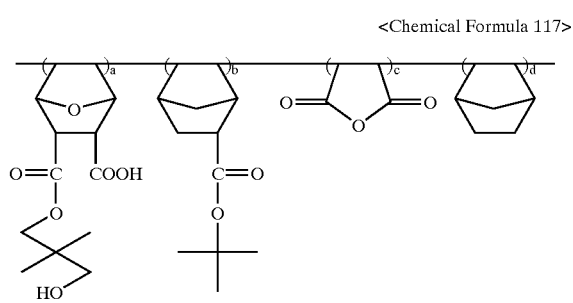

EXAMPLE 32

Synthesis of poly(oxabicyclo[2,2,1]hept-5-ene-2-carboxylic acid-3-(2-ethoxy)ethanol carboxylate/tert-butyl-5-norbornene-2-carboxylate/maleic anhydride/norbornene)

The procedure of Example 26 is repeated but using oxabicyclo[2,2,1]oct-5-ene-2-carboxylic acid-3-(2-ethoxy)ethanol carboxylate as a reactant, instead of oxabicyclo[2,2,1]oct-5-ene-2-carboxylic acid-3-hydroxyethyl carboxylate to obtain the compound represented by following Chemical Formula 118 as a colorless solid (10.7 g/yield: 39%).

<Chemical Formula 118>

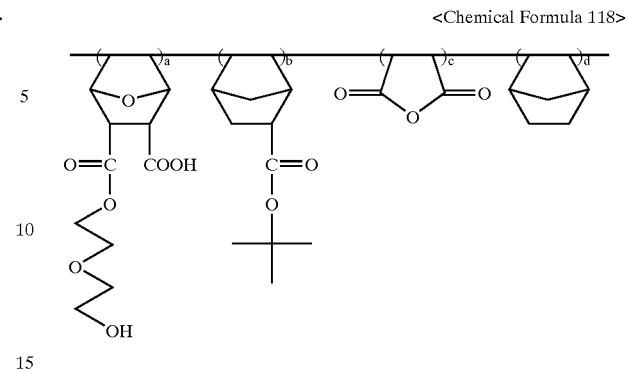

In the Examples described above, petroleum ether or diethyl ether is employed as a solvent for crystallization. Alternatively, alcohols such as methanol, ethanol and isopropanol may be employed.

Preparation of Photoresist Composition and Formation of Photoresist Pattern

EXAMPLE 33

10 g of poly(5-norbornene-2-carboxylic acid-3-(2,2-diethyl)-hydroxypropyl carboxylate/tert-butyl 5-norbornene-2-carboxylate/maleic anhydride) obtained from the Example 15 is dissolved in 40 g of 3-methoxymethyl propionate, and triphenylsulfonium triflate or dibutyl naphthyl sulfonium triflate(0.01–1 g) is added thereto as a photoacid generator. After stirring, the resultant mixture is filtered through a 0.10 μm filter to obtain a photoresist composition. The photoresist composition thus obtained is coated in about 0.3 μm thickness on a surface, and exposed to light by using 193 nm of ArF light source. Then the photoresist is post-baked, and the semiconductor element is impregnated in 2.38% aqueous tetramethylammonium hydroxide (TMAH) solution to be developed and thus 0.13 μm L/S pattern is obtained.

EXAMPLE 34

The procedure of Example 33 is repeated but using the photoresist copolymer obtained from the Example 16 instead of that obtained from the Example 15 and thus a 0.13 μm L/S pattern is obtained.

EXAMPLE 35

The copolymer obtained from Example 19 (10 g) and triphenylsulfonium triflate (0.12 g) as a photoacid generator are dissolved in ethyl 3-ethoxypropionate solvent (60 g), and the resultant mixture is filtered through a 0.1 μm filter to prepare a photoresist solution. The photoresist solution thus prepared is spin-coated on a silicon wafer, and soft-baked at 110° C. for 90 seconds. After baking, the wafer is irradiated with light exposure energy of 0.1 to 10 mJ/cm² by using an ArF laser exposer, and the wafer is post-baked again at 110° C. for 90 seconds. When the post-baking is completed, it is developed in 2.38 w % aqueous TMAH (tetramethylammonium hydroxide) solution for 40 seconds, to obtain a 0.11 μm L/S pattern.

EXAMPLE 36

The procedure according to Example 35 is repeated but using the same amount of the copolymer obtained from Example 20 instead of the copolymer of Example 19, to obtain 0.13 μm L/S pattern.

EXAMPLE 37

The procedure according to Example 35 is repeated but using the same amount of the copolymer obtained from Example 21 instead of the copolymer of Example 19, to obtain a 0.13 μm L/S pattern.

EXAMPLE 38

The procedure according to Example 35 is repeated but using the same amount of the copolymer obtained from Example 22 instead of the copolymer of Example 19, to obtain a 0.13 μm L/S pattern.

EXAMPLE 39

The procedure according to Example 35 is repeated but using the same amount of the copolymer obtained from Example 23 instead of the copolymer of Example 19, to obtain a 0.13 μm L/S pattern.

EXAMPLE 40

The procedure according to Example 35 is repeated but using the same amount of the copolymer obtained from Example 24 instead of the copolymer of Example 19, to obtain a 0.13 μm L/S pattern.

EXAMPLE 41

The procedure according to Example 35 is repeated but using the same amount of the copolymer obtained from Example 25 instead of the copolymer of Example 19, to obtain a 0.12 μm L/S pattern.

EXAMPLE 42

The procedure according to Example 35 is repeated but using the same amount of the copolymer obtained from Example 26 instead of the copolymer of Example 19, to obtain a 0.12 μm L/S pattern.

EXAMPLE 43

The procedure according to Example 35 is repeated but using the same amount of the copolymer obtained from Example 27 instead of the copolymer of Example 19, to obtain a 0.11 μm L/S pattern.

EXAMPLE 44

The procedure according to Example 35 is repeated but using the same amount of the copolymer obtained from Example 28 instead of the copolymer of Example 19, to obtain a 0.13 μm L/S pattern.

EXAMPLE 45

The procedure according to Example 35 is repeated but using the same amount of the copolymer obtained from Example 29 instead of the copolymer of Example 19, to obtain a 0.13 μm L/S pattern.

EXAMPLE 46

The procedure according to Example 35 is repeated but using the same amount of the copolymer obtained from Example 30 instead of the copolymer of Example 19, to obtain a 0.12 μm L/S pattern.

EXAMPLE 47

The procedure according to Example 35 is repeated but using the same amount of the copolymer obtained from Example 31 instead of the copolymer of Example 19, to obtain a 0.13 μm L/S pattern.

EXAMPLE 48

The procedure according to Example 35 is repeated but using the same amount of the copolymer obtained from Example 32 instead of the copolymer of Example 19, to obtain a 0.13 μm L/S pattern.

What is claimed is:

1. A photoresist monomer represented by the following Chemical Formula 2

<Chemical Formula 2>

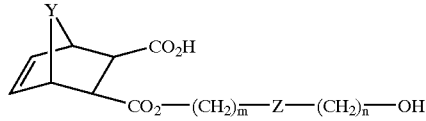

wherein

Y is oxygen;

Z is a moiety of the formula —C($R_1$)($R_2$)— or oxygen;

$R_1$ and $R_2$ are independently H or an ($C_1$–$C_5$) alkyl; and m and n are independently 0 or an integer of 1 to 5.

2. A photoresist monomer according to claim 1, wherein said photoresist monomer is selected from the group consisting of oxabicyclo[2,2,1]-hept-5-ene-2-carboxylic acid-3-hydroxyethyl carboxylate;

oxabicyclo[2,2,1]hept-5-ene-2-carboxylic acid-3-hydroxypropyl carboxylate;

oxabicyclo[2,2,1]hept-5-ene-2-carboxylic acid-3-hydroxybutyl carboxylate;

oxabicyclo[2,2,1]hept-5-ene-2-carboxylic acid-3-hydroxypentyl carboxylate;

oxabicyclo[2,2,1]hept-5-ene-2-carboxylic acid-3-(2-ethyl-2-hydroxymethyl)butyl carboxylate;

oxabicyclo[2,2,1]hept-5-ene-2-carboxylic acid-3-(2,2-dimethyl)hydroxypropyl carboxylate; and oxabicyclo[2,2,1]hept-5-ene-2-carboxylic acid-3-[2-(2-hydroxyethoxy)ethyl]carboxylate.

3. A method for synthesizing a photoresist monomer represented by the following Chemical Formula 1 comprising;

(a) dissolving a di-alcohol compound in an organic solvent;

(a) adding an acid catalyst or a base to the resultant solution with stirring; and (a) adding an anhydride compound to the resultant solution to obtain a compound of Formula 1:

<Chemical Formula 1>

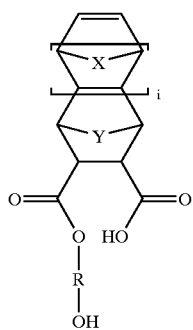

wherein,
R is substituted or non-substituted linear or branched ($C_1$–$C_{10}$) alkyl, substituted or non-substituted ($C_1$–$C_{10}$) ether, substituted or non-substituted ($C_1$–$C_{10}$) ester, or substituted or non-substituted ($C_1$–$C_{10}$) ketone;
X and Y are independently $CH_2$, $CH_2CH_2$, oxygen or sulfur; and
i is 0 or an integer of 1 to 2.

4. A method according to the claim 3, wherein said anhydride compound is 5-norbornene-2,3-dicarboxylic anhydride or exo-3,6-epoxy-1,2,3,6-tetrahydrophthalic anhydride.

5. A method according to the claim 3, wherein said di-alcohol compound is selected from the group consisting of ethylene glycol, 1,3-propanediol, 1,4-butanediol, 1,5-pentanediol, 2,2-diethyl-1,3-propanediol, 2,2-dimethyl-1,3-propanediol and diethylene glycol.

6. A method according to the claim 3, wherein said organic solvent is selected from the group consisting of tetrahydrofuran, dimethylformamide, dioxane, benzene and toluene.

7. A method according to the claim 3, wherein said base is selected from the group consisting of NaH, KH, $CaH_2$, $Na_2CO_3$ and LDA (lithium diisopropylamide).

8. A method according to the claim 3, wherein said acid is selected from the group consisting of sulfuric acid, acetic acid and nitric acid.

9. A method for synthesizing the photoresist monomer represented by Chemical Formula 2 below, comprising;
(a) reacting a maleic anhydride and a di-alcohol compound in the presence of an acid catalyst, as shown in Reaction Scheme 1 below; and
(b) performing a Diels-Alder reaction with the resultant product, as shown in Reaction Scheme 2 below:

<Chemical Formula 2>

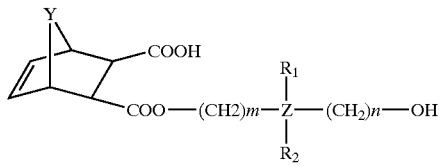

<Reaction Scheme 1>

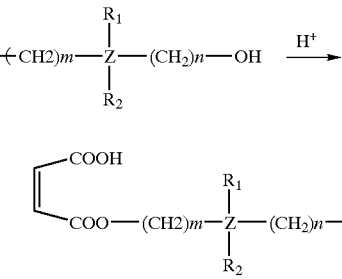

<Reaction Scheme 2>

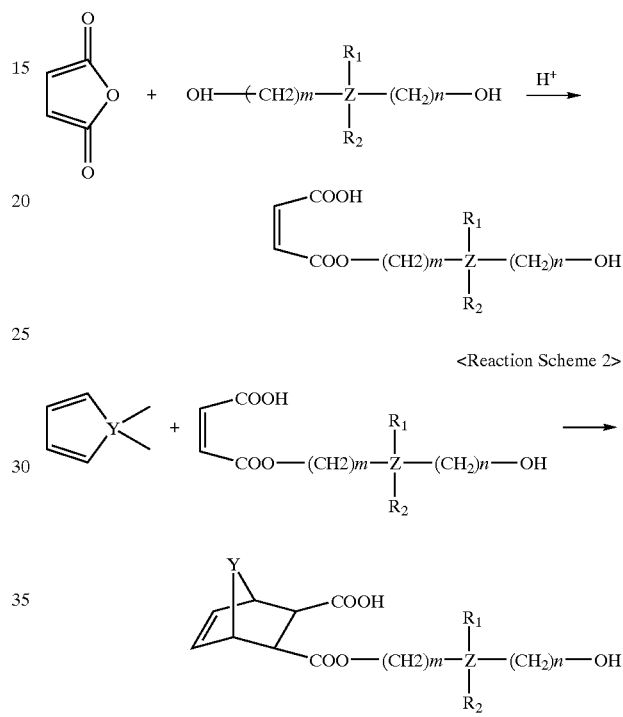

wherein,
Y is $CH_2$, $CH_2CH_2$, oxygen or sulfur;
Z is carbon or oxygen;
$R_1$ and $R_2$ are independently H or an ($C_1$–$C_5$) alkyl; and
m and n are independently 0 or an integer of 1 to 5.

* * * * *